United States Patent [19]

Nickel et al.

[11] 4,371,836

[45] Feb. 1, 1983

[54] DEVICE FOR MEASURING THE LOCATION, ATTITUDE AND/OR CHANGE OF LOCATION OR, RESPECTIVELY ATTITUDE OF A RIGID BODY IN SPACE UTILIZING TWO SETS OF FOUR PARALLEL ANTENNAS FOR CONCENTRATING THE FIELD LINES

[75] Inventors: Bernd Nickel, Lorsch; Wolfgang Schorr, Lautertal, both of Fed. Rep. of Germany

[73] Assignee: Siemens Aktiengesellschaft, Berlin & Munich, Fed. Rep. of Germany

[21] Appl. No.: 100,146

[22] Filed: Dec. 4, 1979

[30] Foreign Application Priority Data

Dec. 6, 1978 [DE] Fed. Rep. of Germany ....... 2852764

[51] Int. Cl.$^3$ .......................... G01B 7/14; A61B 5/10
[52] U.S. Cl. ..................................... 324/207; 128/777
[58] Field of Search ............... 324/207, 208, 244, 260; 340/648; 128/653, 665, 777, 782

[56] References Cited

U.S. PATENT DOCUMENTS

| 3,027,951 | 4/1962 | Knapp et al. | 324/207 |
| 3,439,358 | 4/1969 | Salmons | 128/653 |
| 3,652,927 | 3/1972 | Uemura | 324/208 |
| 4,197,855 | 4/1980 | Lewin | 128/653 |

Primary Examiner—Gerard R. Strecker
Assistant Examiner—Walter E. Snow
Attorney, Agent, or Firm—Hill, Van Santen, Steadman, Chiara & Simpson

[57] ABSTRACT

In an exemplary embodiment, a field generator preferably a magnetic field generator which generates a defined irregular field is arranged directly on the body or at an interval thereto, pickups independent of the body are arranged at an interval from the field generator, said pickups having field-flux-dependent sensor elements for sensing a field flux or, respectively, a change of field flux during a measurement, and an electronic circuit obtains and evaluates electric signals arising in a field flux or, respectively, a field flux change. The sensor elements of the pickups or, respectively, the reference points of the pickups decisive for sensing the field flux or the change of field flux are arranged in such manner that they form the corner points of a cuboid. Thereby, the field generator is arranged within a space determined by the cuboid. The device is particularly provided for use in dental medicine, namely for sensing the lower jaw movement of a patient.

9 Claims, 6 Drawing Figures

DEVICE FOR MEASURING THE LOCATION, ATTITUDE AND/OR CHANGE OF LOCATION OR, RESPECTIVELY ATTITUDE OF A RIGID BODY IN SPACE UTILIZING TWO SETS OF FOUR PARALLEL ANTENNAS FOR CONCENTRATING THE FIELD LINES

BACKGROUND OF THE INVENTION

The invention relates to a device for measuring and recording the location, the attitude and/or the change of location or, respectively, attitude of a rigid body in space, employing a field generator, preferably a magnetic field generator, arranged directly at or at a distance from the body, said generator generating a defined irregular field, with pickups independent of the body arranged at a distance from the field generator, said pickups having field flux-dependent sensor elements for sensing the field flux or, respectively, a change of field flux during a measurement, and an electronic device for receiving and evaluating electric signals arising due to a field flux or, respectively, a change of field flux.

A device of this type is proposed in the German patent application No. P 28 14 551 in which a V-shaped permanent magnet is provided as the field generator and six bar-shaped magnetic flux pickups are provided for sensing the field flux or, respectively, a change of field flux. The magnetic flux pickups are arranged by pairs in three planes that are perpendicular to one another; thus, three surfaces which are perpendicular to one another are formed by means of their arrangement. The entire pickup system is arranged so as to be laterally offset from the patient. Because of the asymmetrical arrangement of the system, nonlinear signals derive which, in order to be evaluatable at all, must be linearized in an electronic manner with a corresponding circuit outlay. Operation of the device, moreover is too complicated and requires too much time for the physician in view of the alignment of the magnetic field pickups on the head of the patient and with respect to the null balance of the electronics. Moreover, the balance of the linearization amplifier is problematic because an inprecision caused, for example, by means of a temperature drift, has an effect on the sensitivity and, thus, on the reproduceability of the signals obtained because of the nonlinear characteristic curve of the sensor elements (Hall generators as a rule) being employed, which the pickups contain.

SUMMARY OF THE INVENTION

The object of the invention is to specify a better and simpler device of the above type which, in contrast thereto, in particular requires less circuit outlay for the signal evaluation and is simpler in terms of operation, so that the physician can easily carry out the adjustment of the pick-ups as a nontechnician.

This object is inventively achieved in a device of the type initially cited in that the sensor elements or, respectively, the reference locations of the pickups which are decisive for sensing the field flux or the change of field flux are arranged in such manner that they form the corner points of a cuboid and in that the field generator is arranged within the space determined by means of the corner points of the cuboid. The arrangement proposed according to the invention is symmetrically designed so that a simpler circuit outlay for evaluating the signals gained by the pickups can be achieved. Moreover, it is possible to arrange the magnetic flux pickups at the sides of the patient's head, so that access to the mouth of the patient remains largely unobstructed.

Advantageous embodiments and further developments of the invention are defined in the subclaims. In the following, an exemplary embodiment of the invention is explained in greater detail on the basis of the accompanying sheets of drawings; and other objects, features and advantages will be apparent from this detailed disclosure and from the appended claims.

DETAILED DESCRIPTION

Figure 1:
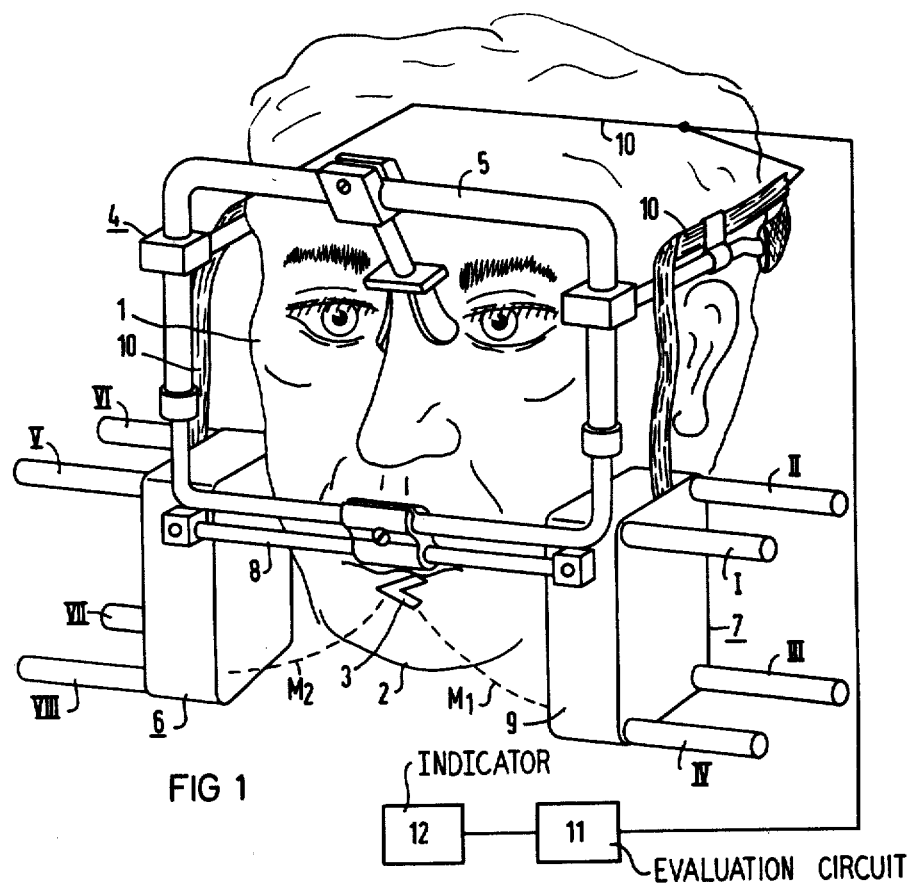
FIG. 1 is a somewhat diagrammatic perspective view showing the inventive device applied to the head of a patient.

In a graphical representation, FIG. 1 shows the inventive device in a particularly advantageous use, namely in dental medicine, for determining the position, the attitude and/or a change of position or, respectively, attitude of a point of the lower jaw of a patient. In the figure, the head of a patient is designated with reference numeral 1 and his lower jaw is referenced with 2. Reference numeral 3 indicates a permanent magnet serving as field generator which is secured intraorally at any desired location of the lower jaw by means of suitable bonding or adhesive agents (for example, moulding compound). The magnetic field generator 3 consists of two bar magnets of like dimensions as are described in greater detail in the German patent application No. P 27 15 106. The angle of aperture between the two bar magnets amounts to approximately 90°. The bar magnets are relatively small; they have an approximate length of three millimeters (3 mm) and a cross-section of approximately one millimeter by one millimeter (1 mm square). The magnetic field generator 3 generates two irregular, nonrotational-symmetrical magnetic fields $M_1$ and $M_2$ indicated in the drawing by means of broken lines.

Outside of the mouth of the patient, there is situated a magnetic flux pickup arrangement 4, essentially consisting of a frame 5 supported on the head of the patient 1 and of a pickup system with respective pickup blocks 6 and 7 located to the left and right of the lower jaw. The frame 5 is designed in a known manner as a combined eyeglass or head frame and contains a plurality of joints not illustrated in greater detail for adapting it to the various head configurations of a patient. The two pickup blocks 6, 7 are rigidly connected to one another by means of a rod 8 connected to the frame 5.

Each of the pickup blocks 6, 7 contains four magnetic flux pickups I through VIII, which are mounted in respective synthetic housings such as indicated at 9 in such manner that they respectively lie parallel to one another. The signals picked up by the magnetic flux pickups I through VIII are supplied via lines 10 to an electronic evaluation circuit 11 and are relayed from there to a suitable indicator device 12.

Figure 2:
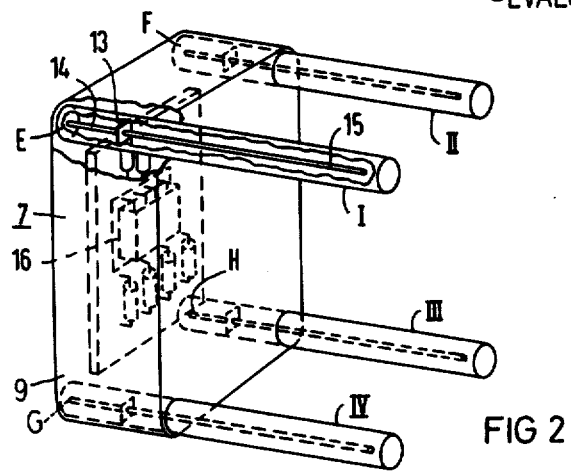
FIG. 2 is a perspective view of a part of the pickup system of FIG. 1 with a portion broken away to show internal construction.

On the basis of the magnetic flux pickup block 7, FIG. 2 shows the arrangement of the magnetic flux pickups I through VIII. Each magnetic flux pickup contains a lamella-shaped Hall generator 13 serving as a sensor element at whose effective surface (referenced with 24 in FIG. 3) antenna bars 14, 15 consisting of Mumetal of different length lie at the respective sides. The signals picked up by the magnetic flux pickups I through VIII, that is, by the Hall generators 13 are supplied to the electronic unit 11 as amplified via the preamplifier 16 (FIG. 2) arranged in the housing 9. A reduction of the number of lines 10 to the electronic unit 11 can be achieved by means of the arrangement of a preamplifier such as 16 in the two housings 9 and 10.

Figure 3:
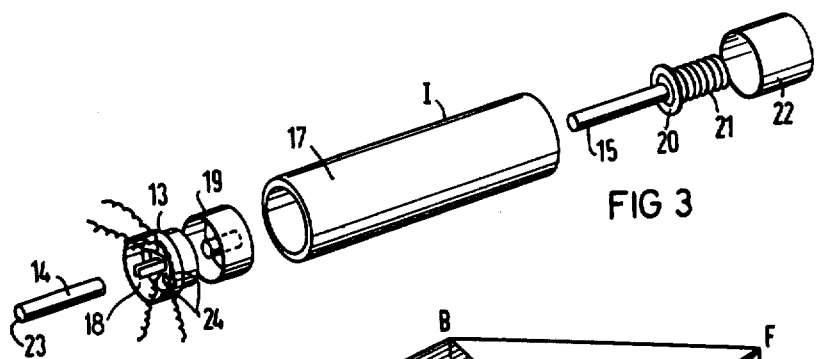
FIG. 3 shows a magnetic flux pickup of the pickup system illustrated in FIG. 2 in an exploded perspective representation.

In an exploded representation, FIG. 3 shows the construction of the bar-shaped magnetic-flux pickups on the basis of the magnetic flux pickup I. The pickup contains a sleeve 17 of nonferromagnetic material, preferably of plastic, into which a support part consisting of two nonferromagnetic parts 18, 19 for the Hall generator 13 is inserted. The two support parts 18, 19 are provided with appropriate bores for guiding the shorter antenna bar 14 on the one hand and, on the other hand, the longer antenna bar 15. In their connected state, the support parts 18 and 19 are guided in the sleeve 17 so as to be longitudinally movable. A nonferromagnetic disk 20 is secured to the antenna bar 15, against which disk a nonferromagnetic compression spring 21 presses, which compression spring presses with its other end against the front face of a nonferromagnetic inspection plug 22 rigidly arranged in the sleeve 17 in the assembled state. The arrangement has the result that the pickup system including the two antennas 14 and 15 and the Hall generator 13 mounted in the parts 18 and 19 is pressed toward the head of the patient. Thus, the end 23 of the antenna bar 14 facing the housing 9 presses against a surface of the housing 9 which is directly adjacent to the head of the patient. The fixed point thereby resulting is referenced in FIG. 2 with E for the pickup I of the pickup block 7. The fixed points F, G and H are assigned to the pickups II, III and IV, and by analogy the points A through D are assigned to the remaining pickups V through VIII, FIG. 1; see FIG. 4. As a result of the resilient arrangement of the parts, the antenna bars 14 and 15 are pressed against the effective surfaces 24, FIG. 3 of the lamellae-shaped Hall generators, whereby the antenna sensitivity is increased.

Figure 4:
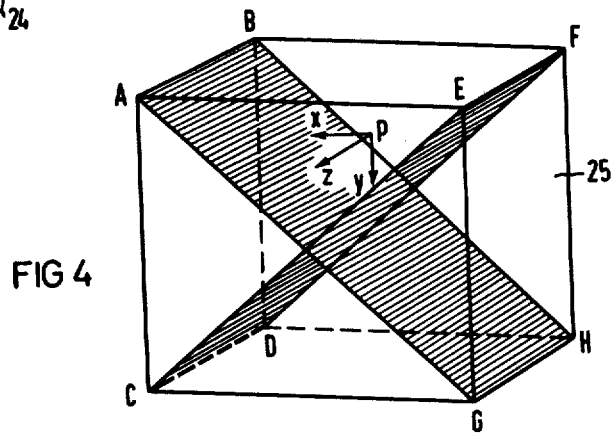
FIG. 4 is a perspective representation of the cuboid formed by means of the corner points of the individual pickups.

Due to the symmetrical arrangement of the Hall generators 13 in the manner revealed, these or, respectively, the fixed points A through H which are formed by means of the seating of the ends 23 of the antenna bars 14 assigned to the Hall generators 13 against the housings such as 9 form the cuboid referenced in FIG. 4 with 25. The magnetic field generator 3, as can be seen from FIG. 1, is arranged within the space formed by the cuboid 25. Proceeding from a point P assumed to be in this space, in which point the magnetic field generator 3 is situated, due to the symmetrical arrangement of the magnetic field pickups, signals corresponding to the following relationships are obtained at the corner points A through H which are representative for the antenna effect with respect to a translational movement of the lower jaw or, respectively, of the field generator in the three planes x, y and z (with the abbreviation "prop." standing for "proportional"):

$A+B+C+D$ prop. x
$C+D+G+H$ prop. y
$A+E+C+G$ prop. z

By analogy, given a movement in the opposite direction, there ensue:

$E+F+G+H$ prop. $-x$
$A+B+E+F$ prop. $-y$
$B+F+D+H$ prop. $-z$

Figure 5:
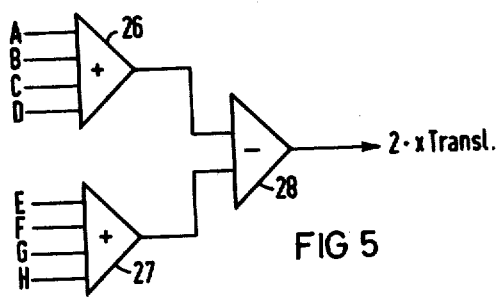
FIGS. 5 and 6 are block diagrams for illustrating the signal evaluation process.

By means of linking the signals in accord with the block diagram according to FIG. 5 by means of a respective summing amplifier 26, 27 and a differential amplifier 28, one obtains an appropriate evaluatable use signal 2x. The analogous case is true for signals y and z.

For the pickup of a rotational movement, the signals from two respective corner point pairs which lie diagonally opposite one another are differentially linked to one another with the complimentary corner point pairs. In FIG. 4, the diagonal surfaces resulting from this for the signal processing of a rotational movement around the z-axis are indicated by shading. Valid for the signal processing is:

$A+B+G+H$ prop. Rot. z
$A+E+D+H$ prop. Rot. x
$B+D+E+G$ prop. Rot. y

Accordingly, there is valid for the opposite direction:

$E+F+C+D$ prop. $-$Rot. z
$B+F+C+G$ prop. $-$Rot. x
$A+C+F+H$ prop. $-$Rot. y

Figure 6:
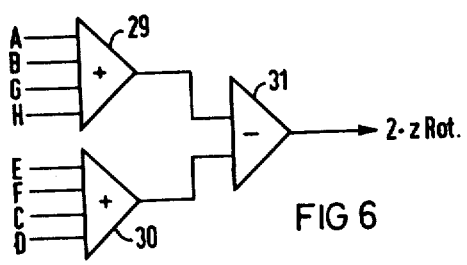

Here, too, the signals are processed via summing amplifiers 29 and 30 and a differential amplifier 31 according to the following relationship:

$(A+E+D+H)-(B+F+C+G)$ prop. 2·Rot. x
$(B+D+E+G)-(A+C+F+H)$ prop. 2·Rot. y
$(A+B+G+H)-(E+F+C+D)$ prop. 2·Rot. z In accord with the signal processing according to FIGS. 5 and 6, direct signals for a translational and a rotational movement can be gained in a simple manner in the three planes x, y and z. In that each corner point can be exploited for a number of surfaces, for example, the corner point A both for the surface A, B, C, D, as well as for the surface A, E, G, C and A, B, E, F, there ensues a simple construction of the entire pickup system. By means of the above principle of differential formation (or: subtraction) of the signals of the respective complimentary plane, moreover, a far greater range of linearity can be created in the previous system where, because of the characteristic of the system magnet/antenna per se, a limited range of linearity was given and, because of that, additional linearization amplifiers were required.

It will be apparent that many modifications and variations may be effected without departing from the scope of the novel concepts and teachings of the present invention.

We claim as our invention:

1. A measuring device for operative association with a rigid body for sensing movement thereof in space, said measuring device comprising a field generator attached to said body for generating a defined irregular field, pickups having field-flux-dependent sensor elements for sensing movement of the field generator relative thereto when the field generator and pickups are mounted for relative movement in accordance with the movement of a rigid body in space during a measurement operation, and an electronic circuit connected to the pickups for obtaining and evaluating electric signals arising from movement of the field generator relative to the field-flux-dependent sensor elements, the sensor elements

(13) of the pickups (I through VIII) having respective elongated antennae (14, 15) concentrating the field lines at the respective sensor elements and having respective ends closest to the field generator (3) forming eight corner points (A through H) of a cuboid (25) with the field generator (3) arranged within the space determined by the eight corner points (A through H) of the cuboid, the sensor elements (13) having respective effective surfaces (24) which are perpendicular to the longitudinal axes of the respective elongated antennae (14, 15), said antennae being arranged in two sets of four elongated antennae, each set of four elongated antennae being arranged with the antennae thereof parallel to one another and the two sets arranged at respective opposite sides of the field generator (3).

2. A device according to claim 1, characterized in that spring elements (21) press the antennae (14, 15) against the effective surfaces (24) of the sensor elements (13).

3. A device according to claim 1, characterized in that antennae comprise an antenna bar (14, 15) at both sides of the sensor elements (13).

4. A device according to claim 1, characterized in that acceptance parts (18, 19) of nonferromagnetic material mount the sensor elements (13) and the elongated antennae (14, 15) with one of the antennae directed toward each of the corner points (A through H) of the cuboid (25), a sleeve (17) mounting the acceptance parts (18, 19) so as to be longitudinally movable, and spring elements (21) pressing the acceptance parts so as to urge the one of the bar-shaped antennae toward its respective corner point (E) of the cuboid (25).

5. A device according to claim 1, characterized in that a housing (9) contains four respective pickups (I through IV), and said electronic circuit comprising an electric preamplifier (16) in said housing for amplifying the electric signals from the pickups.

6. A device according to claim 1, characterized in that, for sensing the translational movement, said electronic circuit comprises a summing amplifier (26) for receiving the signals formed by the sensor elements (13) associated with a respective side (A, B, C, D) of the cuboid (25).

7. A device according to claim 1, characterized in that, for the elimination of external interference fields, said electronic circuit comprises summing amplifiers (26, 27) and a differential amplifier (28) connected with the outputs of said summing amplifiers, with the signals of two respective parallel sides (A, B, C, D and E, F, G, H) being supplied to said summing amplifiers (26, 27) to form two signals at the outputs thereof, the differential amplifier (28), supplying a doubled use signal (2-x-Transl.) and being operative to reject an interference signal.

8. A device according to claim 1, characterized in that, for sensing rotational movement, said electronic circuit comprises a summing amplifier (29) connected to receive the electric signals produced by sensor elements associated with respective corner point pairs (A, B, G, H) of the cuboid lying diagonally opposite one another.

9. A device according to claim 8, characterized in that the electronic circuit comprises a pair of summing amplifiers (29, 30) connected to receive the electric signals produced by sensor elements associated with two respective complementary diagonal surfaces (A, B, G, H and C, D, E, F) and to form two surface signals, said electronic circuit further comprising a differential amplifier (31) connected with said summing amplifiers to supply a doubled use signal (2-z-Rot.) while being operative to reject an interference signal.

* * * * *